Figure 1:
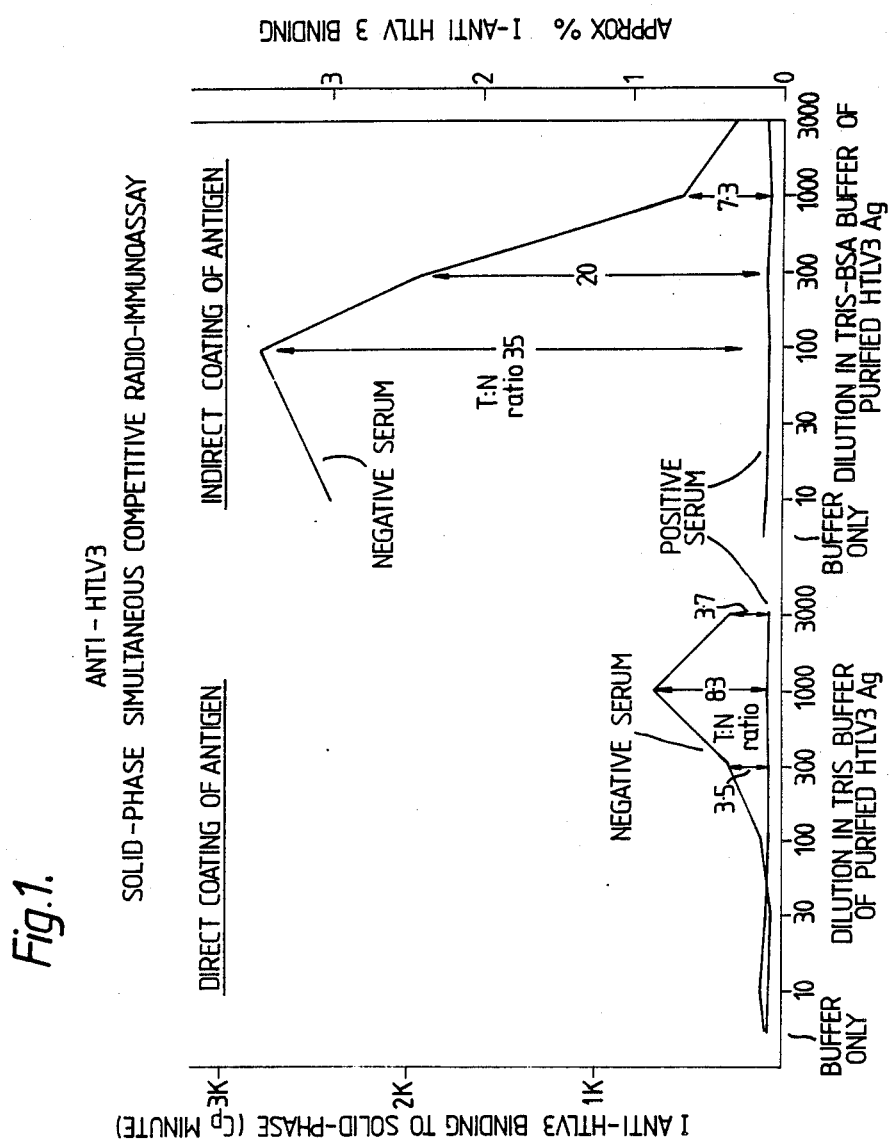

United States Patent [19]

Weiss et al.

[11] Patent Number: 4,912,030
[45] Date of Patent: Mar. 27, 1990

[54] VIRAL ISOLATES AND THEIR USE IN DIAGNOSIS

[75] Inventors: Robin Weiss; Richard Tedder; Rachanee Cheingsong-Popov; Bridget Ferns, all of London, England

[73] Assignee: Institute of Cancer Research, London, England

[21] Appl. No.: 178,892

[22] Filed: Apr. 5, 1988

Related U.S. Application Data

[63] Continuation of Ser. No. 756,604, Jul. 19, 1985, abandoned.

[30] Foreign Application Priority Data

Jan. 15, 1985 [GB] United Kingdom ................ 8500918

[51] Int. Cl.⁴ .......................................... G01N 33/569
[52] U.S. Cl. .......................................... 435/5; 424/89; 424/93; 435/7; 435/93; 435/188; 435/235; 435/810; 436/518; 436/531; 436/543; 436/547; 436/804; 436/808; 436/809; 436/810; 436/815; 436/820; 436/823
[58] Field of Search ................ 435/5, 7, 68, 235-239, 435/93, 188, 810; 436/518-535, 543, 547, 804, 808-813, 815, 820, 823; 424/89, 93

[56] References Cited

U.S. PATENT DOCUMENTS

| | | | |
|---|---|---|---|
| 3,904,367 | 9/1975 | Golibersuch | 436/518 |
| 4,024,235 | 5/1977 | Weetall et al. | 435/5 |
| 4,092,116 | 5/1978 | Giaever | 435/7 |
| 4,126,671 | 11/1978 | House et al. | 435/5 |
| 4,189,464 | 2/1980 | Blumberg et al. | 436/531 |
| 4,241,175 | 12/1980 | Miller et al. | 435/7 |
| 4,382,076 | 5/1983 | Hurni | 435/7 |
| 4,474,877 | 10/1984 | Imagawa et al. | 435/5 |
| 4,520,113 | 5/1985 | Gallo et al. | 436/504 |

FOREIGN PATENT DOCUMENTS

| | | |
|---|---|---|
| 0136798 | 4/1985 | European Pat. Off. . |
| 2016687 | 9/1979 | United Kingdom . |
| 8504897 | 11/1985 | World Int. Prop. O. . |
| 8604423 | 7/1986 | World Int. Prop. O. . |

OTHER PUBLICATIONS

Levy, J. A. et al., Science, 225:840–842, (8—1984).
Analytical Chemistry; 57(7): 773A, 774A, 776A, 778A, (Jun. 1985).
Kalyanaraman, V. S. et al., Science, 225:321–323, (Jul. 1984).
Chemical Abstract, vol. 103, No. 121329H, (1985).
Hazra, D. K. et al., Nucl. Tech. Study Parasit. Infec. Proc. Int. Symp., 1981, pp. 333–347.
Mortimer, P. P. et al., British Medical Journal, vol. 290, pp. 1176–1178, (Apr. 20, 1985).
Clarke, M., Nature, vol. 316:474, (Aug. 8, 1985).
Tedder, R. S. et al., The Lancet, 2 (8395):125–127, (1–1984), (See p. 126, first paragraph).
Cheinsong—Popovl et al., The Lancet 2(8401):477–480, (1984), Cited in Bio. Abstract 79022120.
Wreghitt, T. G. et al., J. Medical Virology, 13(4):361–370, (1984), Cited in Bio. Abstract 78052465.

(List continued on next page.)

Primary Examiner—Christine M. Nucker
Attorney, Agent, or Firm—Oblon, Spivak, McClelland, Maier & Neustadt

[57] ABSTRACT

Samples e.g. transfusion blood, are assayed for antibodies to retroviruses, e.g. AIDS virus, using an insolubilized antigen comprising retrovirus antigens bound to globulin, the globulin itself being bound to an inert solid support; and an immunoglobulin which contains specific antibody to the retrovirus antigens and which is labelled with a revealing label, and the soluble phase is then separated from the insoluble phase and the quantity of revealing label associated with either the soluble or the insoluble phase determined.

The sue of labelled antibody in competition with test sera for binding on the insolublized antigen permits better identification of antibody containing specimens. The retroviruses may be a human T-lymphotropic retrovirus HTLV-I, II or III or a new retrovirus isolate CBL-1 etiologically related to AIDS.

9 Claims, 6 Drawing Sheets

OTHER PUBLICATIONS

Tedder, R. S. et al., J. Medical Virology, 8(2):89–102, (1981) Cited in Bio. Abstract 73053868.

Essex, M. et al., Science, 221(4615):1061–1064, (9-1983).

Kalyanaraman, V. S. et al., Science, 218:571–573, (11-1982).

Barré—Sinoussi, F. et al., Science, 220:868–871, (5-1983).

Haynes, B. F. et al., J. Exp. Med., 157:907–920, (3-1983).

Saxinger, C. et al., Laboratory Investigation, 49(3):371–377, (1983).

De Thé, G. et al., C. R. Acad. Sc. Paris, 297:195–197, (10-1983).

Kalyanaraman, V. S. et al., Virology, 132:61–70, (1984).

Palker, T. J. et al., J. Exp. Medicine, 159:1117–1131, (4-1984).

Schupbach, J. et al., Science 224:607–610, (5-1984).

Schupbach, J. et al., Science 224:503–505, (5-1984).

Sarngadharan, M. G. et al., Science, 224:506–508, (5-1984).

Brun—Vezinet, F. et al., The Lancet (8389):1253–1256, (6-1984).

VIRAL ISOLATES AND THEIR USE IN DIAGNOSIS

This application is a continuation of application Ser. No. 756,604, filed on July 19, 1985, now abandoned.

This invention relates to a new assay for antibody to retroviruses and to new viral isolates for use in the method, and more specifically to the isolation of a virus related to human T-lymphotropic virus and to its use and the use of other retroviruses in the assay of sera to determine the presence of antibodies to retroviruses, particularly those associated with acquired immune deficiency syndrome (AIDS).

The likelihood of acquired immune deficiency syndrome (AIDS) being caused by an infectious agent has been apparent for some years. Symptoms of this disease have been restricted to certain well-defined risk groups in a pattern that strongly suggests an agent transmissible by sexual or blood contact. While the disease was initially detected in the United States of America, there is an increasing prevalence of the disease elsewhere including Europe.

One method by which the disease is believed to be spread is by the transufion of blood that has been donated by donors who are themselves infected with Aids virus. The pooling of donated blood means that if blood given by a donor carrying Aids virus is pooled with samples of blood from other donors, then all of the blood and other products derived from that pool may be contaminated, however large or small the sample. Many blood donors who are carrying Aids virus are unaware of their infection, particularly in the initial phases of the infection, and other infected donors, even if they are aware of their infection, may be reluctant to reveal either that they have the disease or that they belong to a high risk group. There is therefore an increasing demand for relatively simple but completely reliable tests by which samples of blood donated for transfusion purposes can be routinely tested for the presence of Aids virus or antibodies to Aids virus. Blood donations that show up positive in the test can be rejected for transfusion purposes and the contamination of other blood samples by pooling with the contaminated sample can be avoided.

Research into the identification and isolation of the causative agent for Aids has been conducted actively for about 2 years but there is still disagreement between various research workers in the field as to the precise identity and nomenclature of it. A so-called Aids virus isolate was first reported in 1983 by Montagnier and his colleagues in France who named the material "Lymphadenopathy Associated Virus One" (LAV-1). Almost one year later, Gallo and his colleagues in the United States published details of the isolation of another so-called Aids virus which they named "Human T-lymphotropic Virus Type III" (HTLV-III).

We have now been able to isolate, from a lymph node tumor, a human T-lymphotropic retrovirus related to HTLV-III and LAV which we have designated CBL-1. Our CBL-1 material is a stable isolate which can be cultivated in a host cell-line and can be used in an assay for the detection of antibody to Aids virus in serum samples.

Accordingly, the present invention provides human T-lymphotropic retrovirus CBL-1 etiologically related to AIDS.

We have found that CBL-1 can be maintained for prolonged periods of time in a leukaemic T-cell-line designated CCRF-CEM and described by Foley et al, Cancer 18, 522–529 (1965) ad a further feature of the present invention comprises CCRF-CEM cells harbouring our CBL-1 virus.

For confirmation purposes, we have deposited sampls of CCRF-CEM cells harbouring our CBL-1 virus with the National Collection of Animal Cell Cultures (NCACC) at the Public Health Laboratory service Centre for Applied Microbiology and Research, Porton Down, Salisbury, Wiltshire, SP4 OJG England. The NCACC has been designated an International Depository Authority under the Budapest Treaty 1977. Our deposit was made on 11th Jan. 1985 and has been given the Deposit Number 85 01 1101.

Our CBL-1 material was isolated from lymphocytes cultivated from a lymph node tumor biopsy of a British patient undergoing treatment for immunoblastic lymphoma associated with AIDS. Fragments of the biopsy were maintained in a culture medium to which T-cell growth factor was added and after about 2 days, the CCRF-CEM cells were added to the culture which was maintained under conditions such that the primary lymphocytes disappear over the course of about a month while the CCRF-CEM cells profilerate and become chronically infected with the CBL-1 virus.

CBL-1 virus was shown to be related to the previous described isolates of HTLV-III in possessing (a) reverse transcriptase activity with a preference for $Mg^{++}$ cations;

(b) by the morphology of the virus particles visualised by electronmicroscopy;

(c) by indirect immunofluorescence specific for viral antigens in CBL-1 infected CCRF-CEM cells with sera prepared from Aids patients.

(d) by comparison in solid-phase radioimmunoassay with HTLV-III and LAV-1.

The infected cells that we have deposited with the NCACC have been shown to continue to synthesise virus and viral antigens over a period of at least 6 months.

While we have found CCRF-CEM cells to be an ideal host for our CBL-1 virus, we have found that the cells could also be used to harbour similar virus that we have isolated from the peripheral blood of the same patient from whom the lymph node tumor biopsy was taken and similar viruses isolated from other patients infected with Aids related viruses. Thus, we have shown that this cell-line can provide a useful host for the in vitro cultivation of not only our CBL-1 material but other related materials.

According to a further feature of the present invention we provide a method of assaying a biological sample for antibody to retroviruses which comprises bringing the biological sample into contact with (1) an insolubilised antigen comprising retrovirus antigens bound to globulin, the globulin itself being bound to an inert solid support; and (2) an immunoglobulin which contains specific antibody to the retrovirus antigens and which is labelled with a revealing label, and separating the soluble phase from the insoluble phase and determining the quantity of revealing label associated with either the soluble or the insoluble phase.

In a still further feature of the invention we provide a diagnostic test kit comprising (1) a first component which is an insolubilised antigen comprising retrovirus antigens bound to globulin, the globulin itself being bound to an inert solid support and, (2) a second component which is an immunoglobulin which contains specific antibody to the retrovirus antigens and which is labelled with a revealing label.

As indicated above, a major use of CBL-1 is as a component in a test system for the routine testing of transfusion blood to see if it comes from a subject infected with Aids virus. We have developed a system based upon a simultaneous competitive assay using, immobilised CBL-1 antigens as the solid phase, and the test serum as the liquid phase.

More specifically, our simultaneous competitive assay is based upon the immobilisation of the CBL-1 antigen by binding it to a solid phase, preferably via the intermediary of a ligand e.g. an antibody and allowing the binding sites on this immobilised antigen to be competed for by a mixture of test serum antibody and known antibody to the Aids virus which can be identified by a revealing agent. We have found that the most satisfactory results can be achieved when the revealing agent is a radio-label, particularly $^{125}$-I since radioimmuno assays (RIA) based on $^{125}$-I is a system that lends itself particularly well to routine test work in a hospital or blood transfusion laboratory. Of course, other radio-active atoms including radio-active metals can be used in place of $^{125}$-I in accordance with known RIA procedures. Alternatively, use can be made of enzyme-labels in situations where it is desired not to use RIA techniques. A further alternative is to use immunofluorescence to reveal the presence of the known antibody bound to the immobilised antigen.

As indicated above, we have found that the best results are obtained when our CBL-1 antigen is attached to the solid phase through a ligand which is an antibody. Our technique here has been to utilise a high titre human serum taken from someone asymptomatically infected with Aids virus. The ideal serum will have a high titre of antibodies to Aids virus but will come from a patient whose immunoglobulin levels are in the normal range. The solid phase material is conveniently polystyrene which can be used in the form of tubes, beads or preferably plates with a plurality of surface wells or other surface indentations. Gamma-globulin prepared from the selected serum is then coated onto the polystyrene and our CBL-1 antigen is then bound to the globulin-coated polystyrene to form the first component of the diagnostic test kit. This component can be stored wet or dry for several months.

The second component of the test kit comprises the IgG fraction isolated from the test serum and, when revealing is to be done by means of $^{125}$-I, this IgG fraction is radi-labelled with $^{125}$-I according to known techniques.

The diagnostic test kit of the invention can be used by mixing the IgG component with the test serum and then bringing the mixture of IgG and test serum into contact with the insolubilised CBL-1, separating the solid and liquid phases from one another and determining the extent to which the IgG has become bound to the CBL-1. In accordance with simultaneous competitive assays, the greater the extent to which the IgG component of the liquid phase is bound to the solid phase, the smaller the amount of antibody or antigen in the test serum. By selection of appropriate control values, it is therefore possible to have a routine test where, if $^{125}$-I is used as the revealing gent, the test serum can be regarded as free from Aids antibody or antigen provided that the radioactive count on the test sample reaches a predetermined minimum level. Any sample of test serum which causes a radio-active count below the predetermined level to be recorded can therefore be rejected so avoiding possible contamination of transfusion blood with a sample possibly contaminated with Aids virus or antibody.

As an alternative to CBL-1 as the retrovirus antigen in the assay method and diagnostic test kit of the invention, use may be made of other retroviruses. These may be other human retroviruses etiologically related to AIDS such as human T-lymphotropic retrovirus HTLV-III or other human retroviruses such as human T-leukaemia virus, HTLV-II or HTLV-I.

As will be described in more detail below, the indirect binding of human retrovirus antigens to the solid phase via the globulin provides a certain amplification of results and the test format permits a sample, quick and accurate determination of the presence or absence of contamination in blood samples by relatively unskilled and inexperienced technicians.

DESCRIPTION OF THE DRAWINGS

FIGS. 1 and 2 show graphical results of the solid-phase simultaneous competitive radio-immunoassay according to the present invention and compares results obtained by direct and indirect binding of HTLV-III-B to the polystyrene support.

FIG. 3 shows an electron-micrograph at 81,000 times magnification showing CBL-1 particles binding from and located at the boundary of the CCRF-CEM host cells.

FIG. 4 shows the performance of the solid-phase ELISA for anti-HTLV III. The figure shows the optical densities derived from testing a number of clinical area, including those reactive and unreactive for anti-HTLV III, results previously known by radioimmunoassay.

FIG. 5 shows data similar to that of FIG. 4 but this time for anti-HTLV I, determined in a similar one step simultaneous competitive ELISA.

FIG. 6 shows data similar to that of FIG. 4 but for the competitive RIA for anti-HTLV II.

The following Examples are given to illustrate the invention.

EXAMPLE 1

Isolation and Characterisation of CBL-1

Virus CBL-1 was isolated from lymphocytes cultivated from a lymph node tumor biopsy of a British patient undergoing treatment for immunoblastic lymphoma associated with acquired immune deficiency syndrome (AIDS). The lymph node biopsy was cut into small fragments and placed in culture medium composed of RPMI-1640 basal medium supplemented with 10% foetal calf serum and 10 μg/ml phytohaemagglutinin. After 24 hours conditioned medium containing T-cell growth factor harvested from mixed cultures of tonsillar lymphocytes was added, and phytohaemagglutinin removed. At 48 hours after initiation of the culture antiserum to interferon alpha was added. At 48 hours CCRF-CEM cells (hereafter called CEM cells) were also added. CEM cells are a permanently growing leukaemic T-cell line described by Foley et al (1965) Cancer 18: 522–9.

Under the conditions of cocultivation the primary lymphocytes disappeared over the course of 4 weeks culture while the CEM cells proliferated exponentially. The CBL-1 virus produced by the primary lymphocytes infected the CEM cells and after 8 weeks in culture CEM cells were chronically infected with the CBL-1 virus. Maintenance of the CBL-1 infected CEM cells did not require T-cell growth factor or anti-interferon alpha. These CBL-1 infected CEM cells were deposited as indicated above, with the NCACC under the Deposit Number 85 01 11 01.

Figure 3:
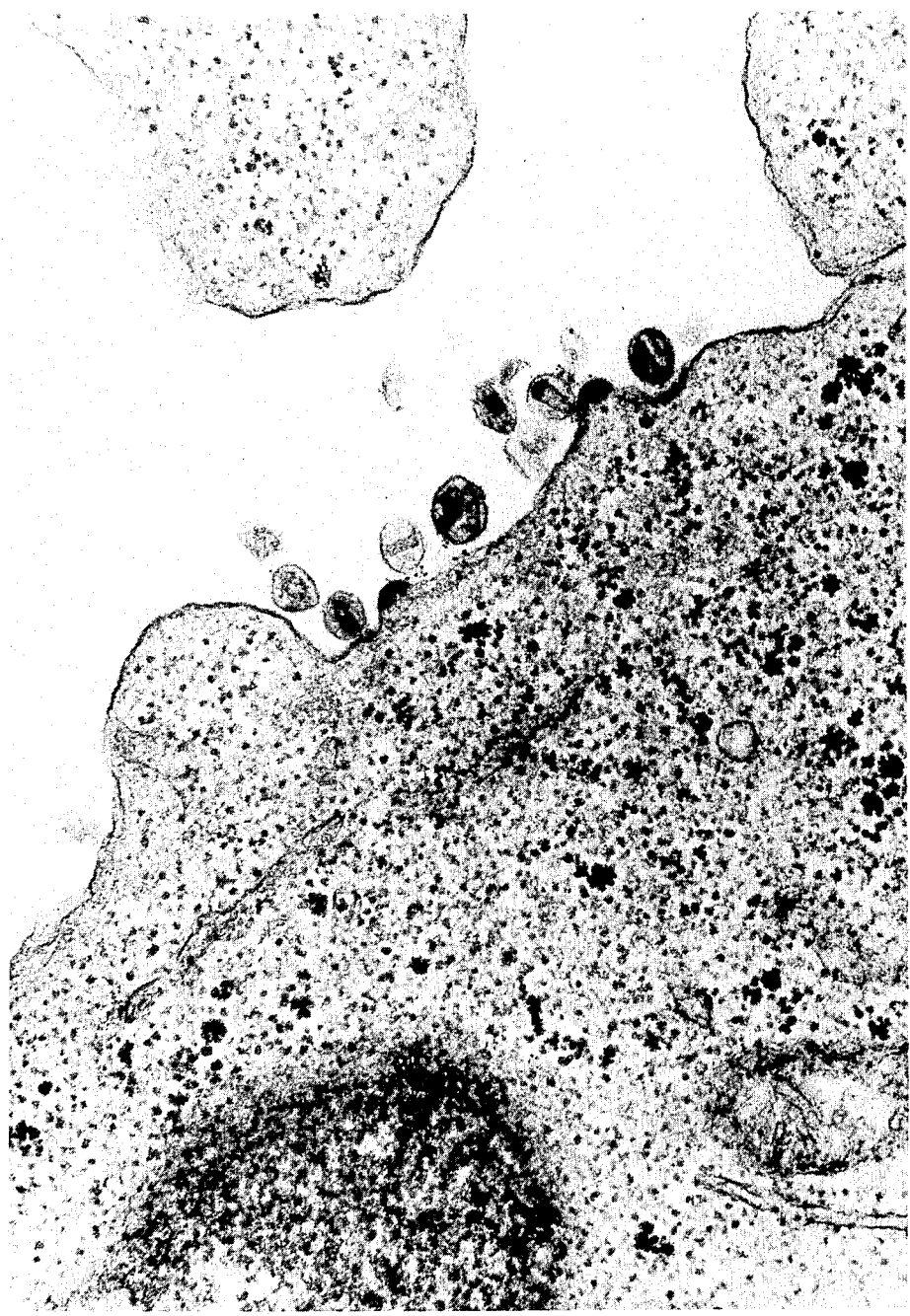

CBL-1 virus was shown to be related to previously described isolates of HTLV-III/LAV in possessing (a) reverse transcriptase activity with a preference for $Mg^{2+}$ cations, by the morphology of the virus particles visualised by electromicroscopy (see FIG. 3) and (b) by indirect immunofluorescence specific for viral antigens in CBL-1 infected CEM cells with sera prepared from Aids patients and by comparison with other aids virus isolates in solid-phase RIA. CEM/CBL-1 cells have continued to synthesize virus and viral antigens over a period of 6 months.

EXAMPLE 2

1. Antigen Preparation

A crude freeze-thaw cell lysate was prepared in the following way. HT-H9 cells infected with HTLV-IIIB were allowed to grow to maximum density in suspension culture. Cultures were cooled to 4° C. and 0.25% v/v β-propiolactone was added for 2 hours. Cells were then spun out of culture fluid and pelletted at low speed. The cell pellet was resuspended in distilled water and subjected to three freeze/thaw cycles. At each cycle the residue of the cell pellet was carefully resuspended. After the third cycle, the extract was made to 0.25% vol/vol with β-propiolactone and kept at 4° C. for 2 hours; it was then warmed to 37° C. for half an hour. During this time the pH was maintained in the region of 7.4. The crude lysate was clarified and stored at −20° C. Prior to use it was diluted in TRIS buffer supplemented with 0.1% BSA and detergent. The choice of detergent and its concentration was important and the use of Tween 20 at 0.1% concentration was found to be optimum, enhancing the activity of the antigen preparation three-fold or sometimes more so. After dilution in TRIS BSA/Tween 20, the antigen was incubated for 30 minutes at 37° C. It is during this step that antigen enhancement occurs.

Antigen preparation in this way may be used to monitor the expression of HTLV-III antigen under various defined culture conditions. The antigenicity may be quantified in solid-phase RIA employing solid-phase anti-HTLV-III and a second reagent, comprising $^{125}$-I anti-HTLV-III. In the final analysis, antigen was used at a dilution which allows a P:N ratio of 10:1 with 1-2% of label binding in the presence of negative sera (see below under assay method). There was a variable shedding of viral antigens into the supernatant fluid of the cells but in relative terms the bulk of detectable antigen was left in the cell pellet. This was true for CBL-1 and for other isolates of HTLV-III carried in CEM cells or HT/H9 cells. There was no constraint or antigen purity (see below) and it was appropriate to maximise antigen expression in the cells. The antigen preparation used here was easy to manufacture, likely to be of a higher yield per volume of cell culture than antigen prepared from supernatant fluid and appears stable at −20° C. It can readily be inactivated by β-propiolactone. The use of Tween 20 would also be expected greatly to reduce the titre of any infectious virus.

2. Antisera

Reagent for the assay was prepared from high-titre human sera taken from persons asymptomatically infected with AIDs retrovirus. The selection of sera for reagent preparation was important. The serum had a high titre of anti-HTLV-III by RIA but came from a patient whose immunoglobulin levels was in the normal range. In practice it is usually necessary to prepare reagents from a small number of sera metting the above criteria and test the performance of the reagents in the assay. In order to render these reagents non-infectious the starting sera were treated by heating at 56° C. for 30 minutes.

(a) Preparation of anti-HTLV-IIIB globulin.

This material was used to purify in situ on a solid phase HTLV-IIIB antigen. There were considerable benefits in this strategy. Globulin from heat treated serum was precipitated twice with 40% saturated ammonium sulphate. This was the simplest reagent for globulin coating though it was possible to use either whole serum or purified IgG. The globulin was used at an optimum dilution which was to be determined by individual titration of the reagent. The solid-phase material was polystyrene in the form of wells and was coated with globulin and spare binding sites were then quenched with an inert protein—in this case 0.1% bovine serum albumin (BSA). The coated and quenched solid phase was stored wet at 4° C. for months; drying gave a more stable product. For coating the solid phase, HT-H9/HTLV-IIIB lysate described above was diluted in TRIS/BSA/Tween buffer to a dilution which, in subsequent testing, allowed 1-2% of the label to bind with a negative serum. Coating was most efficiently achieved by a 2-day incubation of antigen at room temperature in the solid phase followed by storage, wet, at 4° C. until use. Preliminary experiments indicated that the solid phase was stable in this form for several months. However, it can also be dried without significant loss of potency and remains stable for several months.

(b) Preparation of $^{125}$-I and anti-HTLV-IIIB

An ion-exchange chromatography fraction of IgG (0.02 mol/l phosphate buffer, pH 8.0) was made from the selected high-titre human anti-HTLV-IIIB serum. The IgG preparation was labelled with $^{125}$-I to a specific activity of 15 µCi per µg protein. For use, this was diluted to 100 nCi per 100 µl in TRIS containing 2% BSA and 20% normal human serum (NHS) negative for all antibody markers of HTLV-I, II and III.

3. Test Format

The test was based upon the competition of test sera with $^{125}$-I anti-HTLV-IIIB prepared as above. The presence of serum antibody (and presumably also serum antigen) inhibited the binding of label. Serum giving significant inhibition was considered to contain antibody or antigen.

Figure 2:
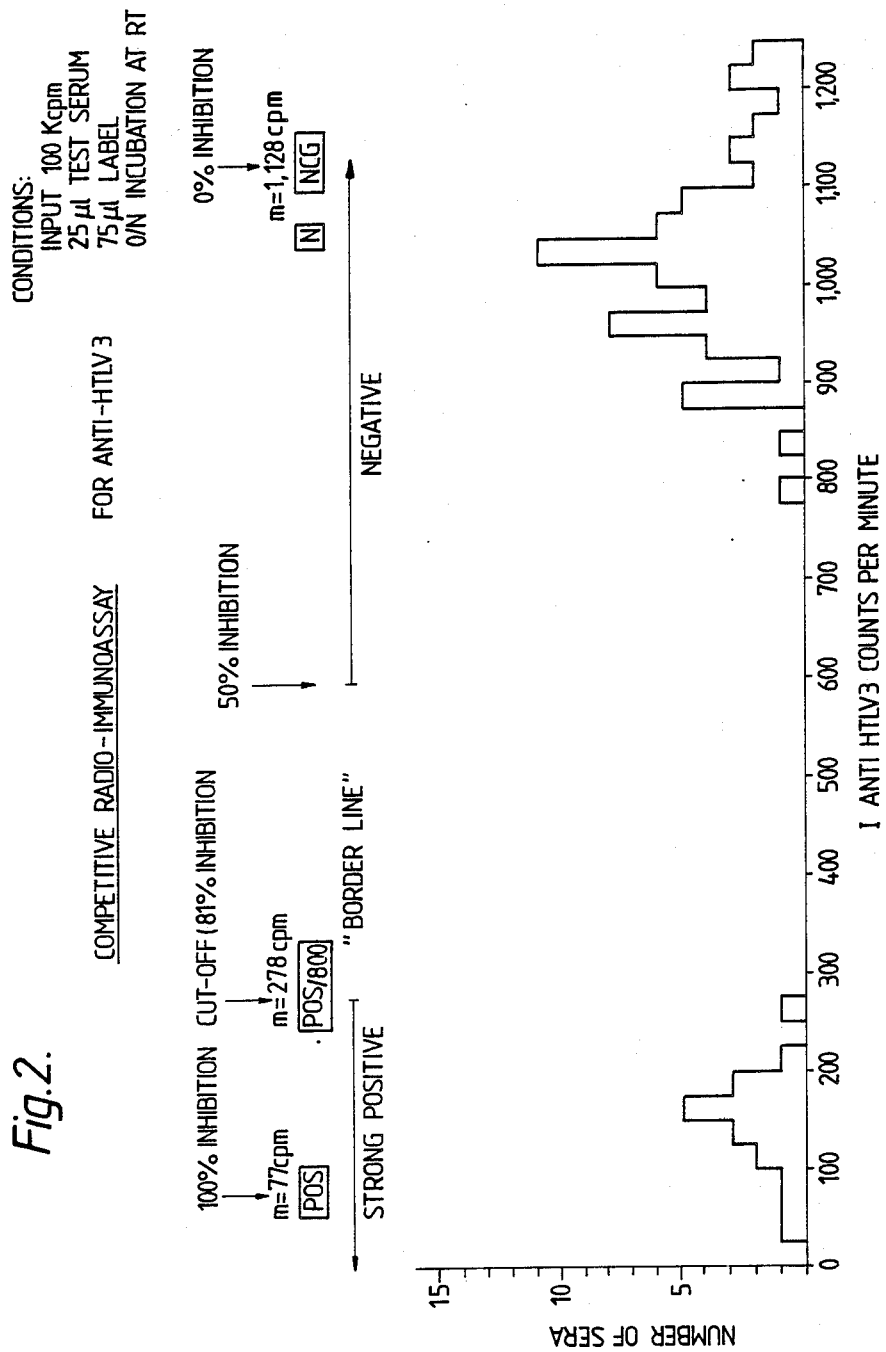

Test samples of undiluted serum were utilised and mixed in the proportion of 25 µl serum and 75 µl of radio-labelled IgG. This mixture was placed in one of the antigen-coated polystyrene wells and incubated overnight at room temperature (15 to 18 hours at 20° C.). Initially, there were 100,000 counts per minute of radioactivity. The use of the coated polystyrene having a plurality of wells means that it was possible to carry out simultaneously tests on a large number of test sera, each serum being tested in a similar manner and being located in identified wells in the solid support. The next morning, the solid support was washed to remove all traces of the liquid phase samples introduced the night before and the radioactivity associated with each of the surface depressions determined in the usual way. The number of counts per minute was measured and the results were illustrated graphically as shown in FIGS. 1 and 2 of the accompanying drawings. FIG. 2 shows how it was possible readily to determine whether the serum was positive or negative as regards the presence of Aids antibody, 600 counts per minute being regarded as the 50% inhibition point so that the great majority of the sera tested where the wells gave a count of between 900 to 1200 can be regarded as seronegative samples. On the other hand, those few sera where the count was in the region of 100 to 200 would be considered seropositive. FIG. 2 shows how substantially all of the test sera fell clearly into the strong positive or negative group, there being very few sera falling in the borderline areas.

FIG. 1 shows, on the right-hand side, the results obtained using a solid-phase prepared by either direct binding of the antigen or by the indirect method described above and specifically shows the considerable difference in results between the negative, serum and the positive serum that contain antibody to the AIDS retrovirus.

The results shown on the left-hand side of FIG. 1 were the results obtained in a comparative test which was carried out in exactly the same way except that the solid-phase comprises the same polystyrene sheet to which a purified AIDS retrovirus preparation was bound directly rather than through a gamma-globulin link. These results show that although it was still possible to distinguish between the negative test sera and the positive test sera, the different between the two, in terms of the difference in binding of radio-activity was very much smaller, thus making it more difficult to distinguish between those borderline cases. Although the results on the left-hand side of FIG. 1 have not been presented in the format of FIG. 2, it can readily be visualised that the closeness of the curves for the positive and negative sera when antigen was directly bound had the effect of reducing very substantially that area in the centre of FIG. 2 which facilitated the identification of the positive and negative sera.

EXAMPLE 3

One step competitive ELISA for anti-CEM/CBL 1

Serum reagents

A human serum containing a high titre of anti-HTLV III was used for the preparation of coating globulin as previously described in Example 2.2. Polystyrene wells with a round bottom configuration were coated with an optimum dilution of globulin and then quenched with an inert protein, in this case 0.1% BSA. The same serum was used as a source of immunoglobulin, which was purified by ion-exchange chromatography on DE 52 as previously described. IgG was coupled with horseraddish peroxidase at an approximate substitution ratio of 3 molecules of horseraddish peroxidase per 1 molecule of IgG.

The performance of the conjugate was determined by incubation over wells previously coated via an indirect antibody with virus antigens derived from HTLV III infected cells and with antigens uninfected cells. The optimum dilution of conjugate was taken as that which gave maximum color binding with the infected cell antigen and minimum colour production with the uninfected cells.

CEM/CBL 1 antigen

Cells persistently infected with CEM/CBL 1 virus were grown up to maximum density in non-adherent stirrer cultures. Stirrer cultures were cooled to 4° C. and then brought to 0.25% volume with $\beta$-propiolactone. After 2 hours incubation at 4° C., the cell pellet was harvested and subjected to freeze thaw and thaw cycles, and then clarified as previously by centrifugation. The tissue culture extract was then treated to a further 2 hour incubation at 4° C. with 0.25% $\beta$-propiolactone and then hydrolised as previously. In this case the diluent for cell disruption and freeze thaw cycling was phosphate buffered saline, supplemented with 0.1% tween 20. Antigen preparations were subsequently titrated on a solid phase coated with high-titre anti-HTLV III globulin, and that dilution which gave an OD 450 nm between 1.0 and 1.2 under conditions defined below was used as a working dilution for subsequent testing.

Optimisation and format of testing

Wells coated with high-titre globulin and subsequently quenched, were incubated with a 100 $\mu$l of optimum dilution of CEM/CBL 1 antigen. After an overnight incubation at room temperature, the antigen extract was washed from the wells which were then dried under conditions were where found to promote stability of immobilised CEM/CBL 1 virus antigens. For testing 25 $\mu$l of antibody positive and negative sera were placed in separate wells, and 75 $\mu$l of ELISA conjugate in detergent-supplemented distilled water added to the wells. The mixture of test serum and conjugate was incubated (immune incubation) in the wells for 1 hour at 45° C. The wells were then washed three times with saline tween (0.8% sodium chloride solution supplemented with 0.1% tween 20). After three washes the wells were filled with saline tween and allowed to soak for 2 minutes at room temperature, after which the washing procedure was repeated with three cycles of washing. Following this 100 $\mu$l of chromogen substrate, in this case tetramethyl-benzidine (TMB), were added. After a 20 minute incubation at room temperature the chromogen release was terminated by the addition of 50 $\mu$l of 4 normal sulphuric acid. The colour release was measured spectrophotometrically at 450 nm. The working dilution of any particular CEM/CBL 1 antigen was considered as that dilution which reliably gave an optical density of between 1 and 1.2 with negative serum when used in the ELISA under the conditions defined above.

Results

Figure 4:
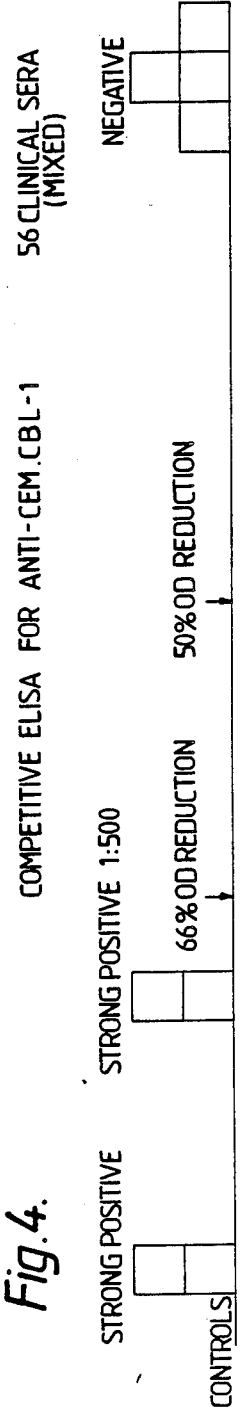
Figure 4:
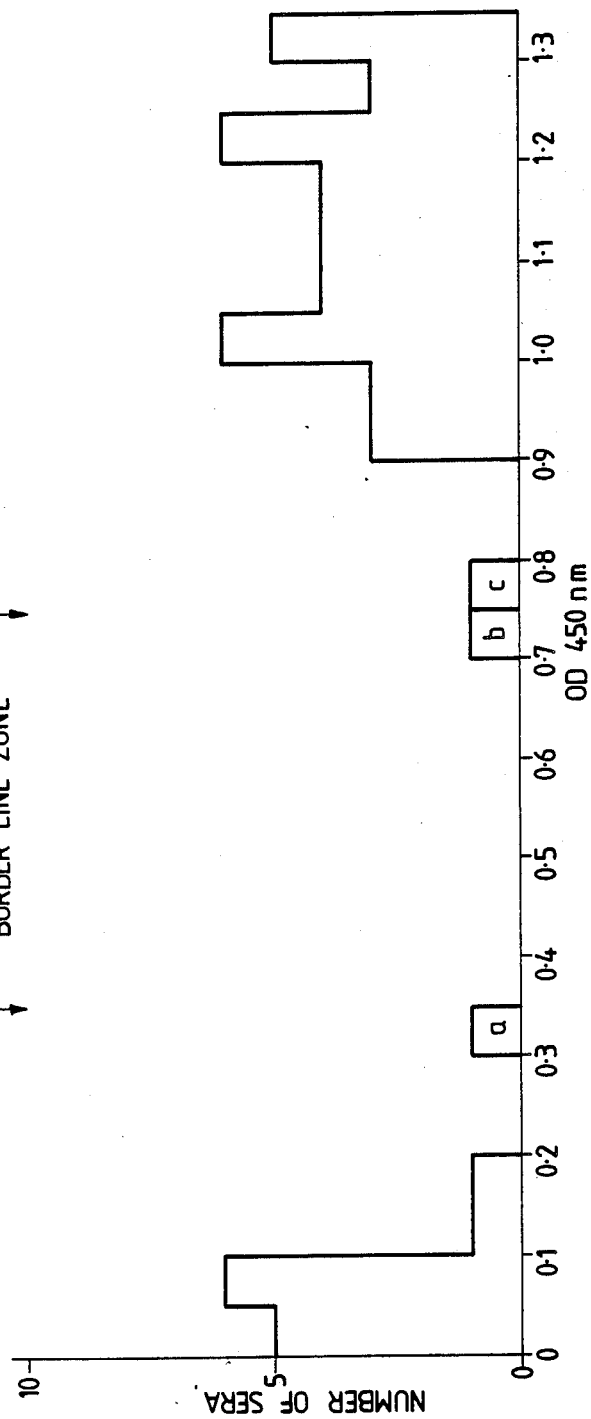

In FIG. 4, the results of testing 56 clinical sera, in this case derived from haemophiliacs treated with commercial and non-commercial FVIII concentrates and homosexuals are shown. As can be seen in the Figure, there was clear separation between sera reactive for anti-CEM/CBL 1 and sera unreactive. In this particular example, the mean optical density of 16 sera reactive for CEM/CBL 1 antibody was 0.085 (0.037 to 0.327) and the mean optical density for 40 sera unreactive for this antibody was 1.16 (0.736 to 1.352). Serum was from a terminally ill AIDS patient and was weakly reactive in IF and direct binding assays. Sera b and c were unreactive on retesting.

Exactly the same format has been used in a survey of Blood Transfusion sera in the United Kingdom. At the present time over 12,000 sera from donors have been tested. 3 sera gave screen test reactions however, on retesting, only one single donor has been found to be reactive. The serum was repeatedly reactive, was titratable, and demonstrated strong reactivity in immunofluorescence against infected but not uninfected cells. The random reactivity of sera which was unrelated to CEM/CBL 1 infection was therefore extremely low. Subsquent experiments on titrating sera reactive for anti-HTLV III demonstrated that the titres were broadly the same when tested in both the CEM/CBL 1 ELISA and the direct assays. This has been confirmed by subsequent examination of sera taken from patients undergoing acute seroconversion following primary HTLV III infection. Again there was broadly no difference in the level or time of initial reactivity in either the direct binding assay nor the competitive ELISA. Using the same assay, sera from patients with oligo and pan-reactive anti-lymphocyte antibodies, and sera from patients with auto immune disease were unreactive in the competitive ELISA. Taken together, these data indicate that the specificity and sensitivity of this competitive ELISA for antibody to the AIDS related retrovirus are high.

EXAMPLE 4

One Step Competitive ELISA for anti-HTLV I

Figure 5:
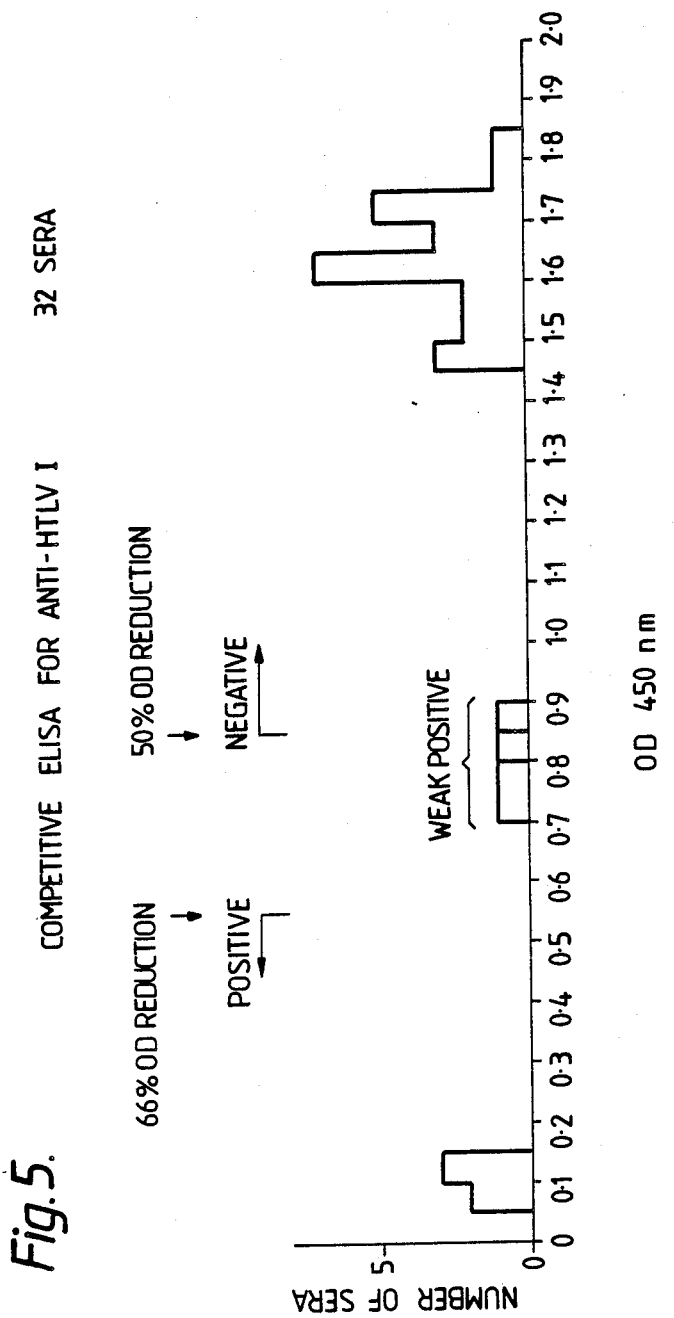

Sera and reagents were selected and prepared in same way as for the CEM/CBL 1 immunoassay of Example 3 with the exception that cells infected with HTLV I were used for antigen preparation, and sera from patients infected with HTLV I were used as a source of reagents. In FIG. 5 the optical density given by 32 clinical sera, including 3 known weak positive controls is shown. Clear differentiation occurred between reactive and unreactive sera, with the mean optical density of 5 sera reactive for this antibody being 0.099 (0.060 to 0.129) and the mean optical density for 24 sera unreactive for this antibody being 1.64 (1.48 to 1.83). The test was robust and the conditions could be varied but in practice it was decided to optimise on an immune incubation of 1 hour at 45° C. This was in parallel for those conditions for CEM/CBL 1 antibody detection.

This test has been used in the same format to screen over 1000 unselected British blood donors and no reactive sera were identified. In contrast, selective screening of some 75 African and Carribean origin donors identified a single seropositive first-time donor.

EXAMPLE 5

One Step Competitive RIA for anti-HTLV II

Sera from patients infected with anti-HTLV II were used as a source for coating globulin and as a source of IgG. Cells infected with HTLV II were used as an antigen source. These reagents were selected and prepared in the same manner as described previously in Example 2 for the anti-HTLV III RIA. Using reagents in exactly the same format as described for the anti-HTLV III RIA, clear differentiation was achieved between sera reactive and unreactive for anti-HTLV II.

| Sera | | Binding $^{125}$I-anti-HTLV II IgG* | 50% end point |
|---|---|---|---|
| Mean negative | | 1,420 | — |
| Drug addicts | IH | 155 | 1,000 |
| | RG | 143 | 200 |
| | MA | 137 | 100 |
| Homosexuals | IF | 874 | — |

| Sera | | Binding $^{125}$I-anti-HTLV II IgG* | 50% end point |
|---|---|---|---|
| | MC | 829 | — |

*c.p.m.
**sera from i.v drug abusers.
anti-HTLV I - positive.

Figure 6:
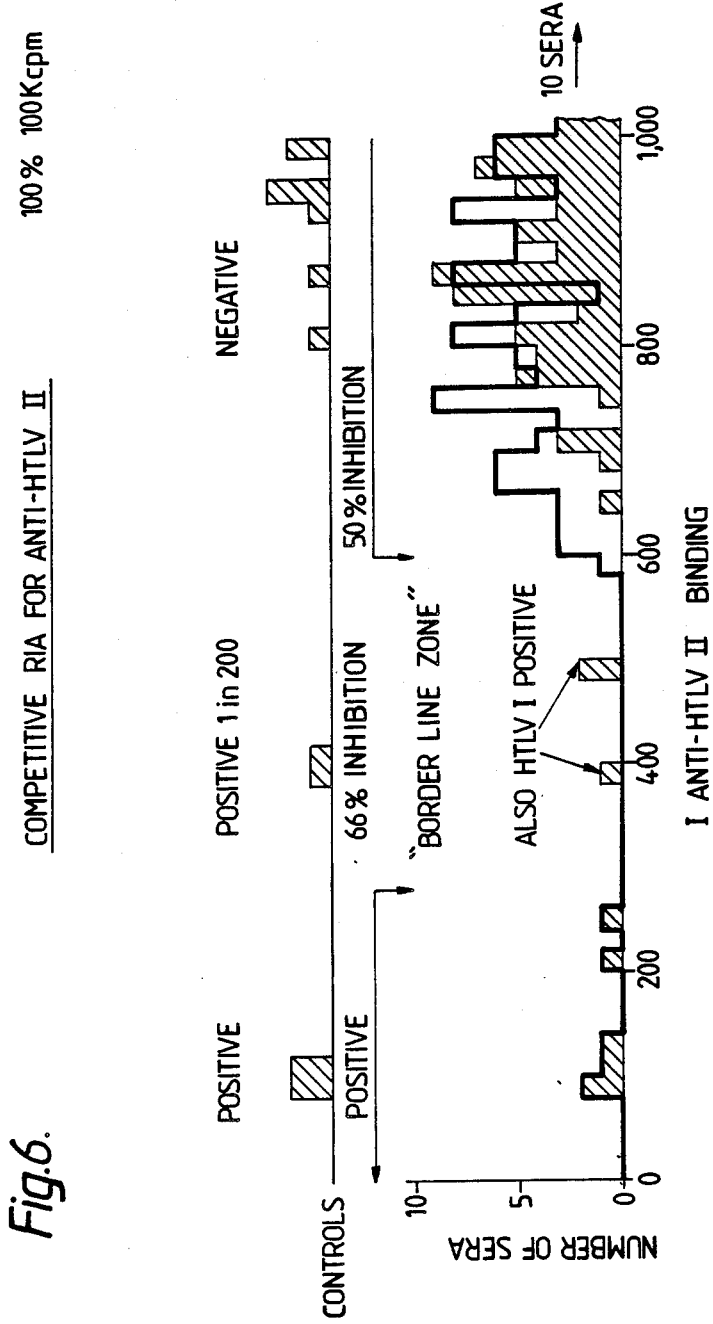

FIG. 6 shows the data from testing 121 drug addict and homosexual sera for anti-HTLV II. Superimposed are the reactivities of sera from HTLV III-infected homosexuals with AIDS and PGL (shown cross hatched).

There was some crossing between sera containing anti-HTLV I and sera containing anti-HTLV II. Sera reactive for anti-HTLV I gave up to but not greater than 50% inhibition of binding (Table), IF and MC (Table above), but sera reactive for anti-HLTV III showed no crossing and di not affect the level of label binding.

In the Examples above, the assay is conducted by a determination of radioactivity or enzyme associated with the solid phase. However, since the radioactivity or enzyme level associated with the starting sera is known, it is also possible to monitor the reduction in radioactive count or enzyme level associated with the liquid phse after the known labelled sera and the test sera have been brought into contact with the solid phase antigen and the reduction in radioactivity or enzyme level of the liquid phase used as a measure of the antibody content of the test sera.

The advantages of the simultaneous competitive assay can be summarised under the following headings.

Antigen Preparation

Although our FIG. 1 relates to the use of purified HTLV-III viruses, the enhanced binding resulting from use of an immobilised antibody allows the use of a crude cell lysate preparation for coating when by itself, such an antigen will not bind directly in any useful way to a solid phase. This step removes the constraint of needing highly purified antigen for production of diagnostic tests and will make their manufacture easier. It is an advantage which is not applicable to direct assays where a whole human globulin coat would give an unavoidable signal with the final anti-human globulin label.

Format

The use of a volume of undiluted serum offers a significant advantage to blood transfusion centres where a need to make an initial dilution would increase the work load. The ratio between serum and radio-label volumes can be varied through the range 1:1 to 1:10 with only little alteration in test performance. The optimum is 1:3, employing 25 μl of serum and 75 μl of radio-label and gives good differentiation between positive and negative sera (FIG. 2). It is also possible to shorten the incubation of the assay. Normally run overnight at room temperature, the test still produces good results when conducted at elevated temperatures and shorter times. An incubation of 2 hours at 45° C. is the optimum for the shortened RIA test and could be recommended for its use in the transfusion service. However, assay times can be shortened to 1 hour or less by the use of an Elisa technique.

Sensitivity

One measure of the sensitivity of any assay for Aids antibody is given by the proportion of sera taken from terminally ill patients with Aids which remain positive. With direct assays it seems that a variable number of patients lose antibody reactivity. This does not happen with the competitive assay, suggesting that the sensitivity of the competitive assay is as good as or better than the other assays currently used.

Specificity

A competitive assay would not be expected to have major problems of false-positive reactivity. Inclusion of lymphocyte membrane antigens into the envelope of HTLV virions certainly leads to false reactivity, as does the presence of aggregates of IgG which stick non-specifically to the solid phase. Such phenomenon do not give rise to reactivity in the competitive assay. Non-specific affects of variable protein concentration can be minimised by selection of an appropriate serum/label ratio (1:3, see above) and by the use of a cut-off of greater than 50% inhibition. Sera which produce an inhibition of label binding equal to or greater than that given by an internal control serum (75% inhibition, Pos/800, FIG. 2) are considered screen-test positive but the testing should be repeated. In view of the low level of false reactivity, expected to be less than 1 in 5,000, it is unlikely that false-positive reactions in the competitive RIA will give such a numerically large problem as they seem to do in the direct assays. This is particularly so where direct assays are performed without a control antigen. It is anticipated that this will be the case in transfusion centres as the use of a control antigen would double the requirement for reagents in the direct assay.

Summary

The combination of simple format, high sensitivity and high specificity makes the competitive assay ideal for use in screening of blood donations and for diagnostic use. In addition, where centres use a direct assay for anti-HTLV-III it may prove better to confirm serum reactivity by re-testing in competitive assay rather than subjecting sera to the more laborious and less sensitive Western Blotting that may be recommended by the FDA in the United States.

We claim:

1. A method of assaying a liquid biological sample for antibody to a retrovirus which comprises bringing the biological sample into contact with
   (1) an insolubilised antigen comprising retrovirus CBL-1 antigen bound to globulin, the globulin being bound to an inert solid support; and
   (2) an immunoglobulin which contains specific antibody to the retrovirus antigen and which is labelled with a label capable of providing a detectable signal, the contacting being for a time and under conditions sufficient for immune complex formation between the sample antibody and the insolubilised antigen, and separating the resulting liquid phase from the resulting solid phase and detecting the quantity of label in either the liquid or the solid phase as a measure of antibody in the sample.

2. A method according to claim 1 wherein the biological sample is serum or plasma from human blood.

3. The method according to claim 2 wherein the retrovirus is human T-lymphotropic retrovirus CBL-1 and wherein the immunoglobulin labelled with the label is immunoglobulin from a human patient asymptomatically infected with the said retrovirus but having a normal immunoglobulin level.

4. A method according to claim 1 wherein the inert solid support is polystyrene.

5. A method according to claim 1 wherein the label is a radioactive label or an enzyme label.

6. A diagnostic test kit comprising
   (1) a first component comprising antigen of a retrovirus CBL-1, said antigen being bound to globulin and the globulin being bound to an inert solid support so as to form an insolubilised antigen, and,
   (2) a second component which is an immunoglobulin which contains specific antibody to said antigen and which is labelled with a label capable of providing a detectable signal.

7. A kit according to claim 6 wherein the retrovirus is human T-lymphotropic retrovirus CBL-1 wherein the immunoglobulin is from a human patient asymptomatically infected with the said retrovirus but having a normal immunoglobulin level.

8. A kit according to claim 6 wherein the label is a radioactive label or an enzyme label.

9. An insolubilised antigen comprising antigen of a retrovirus CBL-1, where the antigen is bound to globulin and the globulin is bound to an inert solid support.

* * * * *